United States Patent [19]

Junino et al.

[11] Patent Number: 5,032,137
[45] Date of Patent: Jul. 16, 1991

[54] P-PHENYLENEDIAMINES, PROCESS FOR PREPARATION THEREOF, DYEING COMPOSITIONS CONTAINING THEM AND CORRESPONDING DYEING PROCESS

[75] Inventors: Alex Junino, Livry Gargan; Alain Genet, Aulnay sous Bois; Gerard Lang, Saint Gratien, all of France

[73] Assignee: L'Oreal, Paris, France

[21] Appl. No.: 583,079

[22] Filed: Sep. 13, 1990

Related U.S. Application Data

[62] Division of Ser. No. 342,578, Apr. 24, 1989, Pat. No. 4,979,961.

[30] Foreign Application Priority Data

Apr. 25, 1988 [FR] France ................................. 8805473

[51] Int. Cl.$^5$ .............................................. A61K 7/13
[52] U.S. Cl. .......................................... 8/410; 8/405; 8/416; 8/428; 8/429; 564/440
[58] Field of Search .................... 8/405, 410, 416, 649, 8/659, 917, 428, 429; 564/440

[56] References Cited

U.S. PATENT DOCUMENTS 4,979,961 12/1990 Junino et al. ........................... 8/410

FOREIGN PATENT DOCUMENTS 3325790 1/1985 Fed. Rep. of Germany .

*Primary Examiner*—Paul Lieberman
*Assistant Examiner*—William S. Parks
*Attorney, Agent, or Firm*—Marshall, O'Toole, Gerstein, Murray & Bicknell

[57] ABSTRACT

The invention relates to p-phenylenediamines of formula:

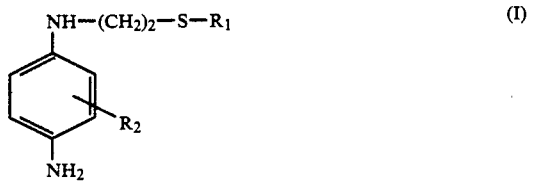

in which $R_1$ denotes an alkyl, hydroxyalkyl or polyhydroxyalkyl radical and $R_2$ denotes a hydrogen atom or an alkyl radical, as well as the corresponding salts with acids, and to the compositions and the process for dyeing keratinous fibers, and especially hair, employing them.

2 Claims, No Drawings

P-PHENYLENEDIAMINES, PROCESS FOR PREPARATION THEREOF, DYEING COMPOSITIONS CONTAINING THEM AND CORRESPONDING DYEING PROCESS

This is a division of application Ser. No. 07/342,578 filed Apr. 24, 1989, now U.S. Pat. No. 4,979,961.

The invention relates to new para-phenylenediamines, to their preparation, and to the compositions and the process for dyeing keratinous fibres employing them.

It is known that, in the oxidation dyeing of keratinous fibers, and especially hair, p-phenylenediamines play a very important part, whether they are used alone or in combination with couplers such as m-phenylenediamines, m-aminophenols or m-diphenols.

In order that an oxidation dye, and especially a p-phenylenediamine, may be selected for hair dyeing, it has to be completely harmless when applied in a hair dye, and the hues imparted to the hair also have to be stable with the passage of time and, in particular, resistant to light, to adverse weather conditions and to shampooing during the period which normally separates two successive dyeings of the hair.

The subject of the present invention is new p-phenylenediamines which, at the same time, on the one hand are completely harmless when applied in a dye for keratinous fibers, and especially hair, and on the other hand offer good stability of the hues obtained with the passage of time, especially good stability to adverse weather conditions, to light and to washing.

The subject of the present invention is also a process for preparing these compounds.

Another subject of the invention consists of the dyeing composition containing at least one para-phenylenediamine of this family.

The subject of the invention is also the new N-substituted p-nitroanilines used in the synthesis of the abovementioned new p-phenylenediamines, as well as their use in direct dyeing of hair.

The subject of the invention is, finally, a dyeing process for keratinous fibers, and especially for human hair, using these para-phenylenediamines.

Other subjects of the invention will become apparent on reading the description and the examples which follow.

The para-phenylenediamines according to the invention are essentially characterized in that they correspond to the formula:

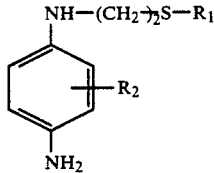

in which $R_1$ denotes an alkyl, hydroxyalkyl or polyhydroxyalkyl radical and $R_2$ denotes a hydrogen atom or an alkyl radical, or the corresponding salts with acids.

Preferred compounds correspond to the general formula (I) in which $R_1$ denotes an alkyl radical containing from 1 to 4 carbon atoms, hydroxyalkyl radical containing from 2 to 4 carbon atoms or polyhydroxyalkyl radical containing 3 or 4 carbon atoms, and $R_2$ denotes a hydrogen atom or an alkyl radical containing 1 to 4 carbon atoms, as well as the corresponding salts with acids.

Preferred salts are chosen from the hydrochlorides, sulphates, tartrates and other cosmetically acceptable salts.

The process for preparing the compounds of formula (I) essentially comprises the following stages:

1/ A p-halonitrobenzene of formula (II):

in which $R_2$ has the meaning defined in the formula (I) and X denotes a halogen atom, is treated with an amine of formula:

$$NH_2(CH_2)_2SR \qquad (IV)$$

in which $R_1$ has the meaning defined in the formula (I), to obtain the p-nitroaniline of formula (III):

2/ The $NO_2$ group of the compound of formula (III) is reduced either by reduction with hydrogen in the presence of a catalyst, or by reduction with iron in acetic acid or zinc in the presence of alcohol and ammonium chloride.

The process for preparing the compounds of the formula (I) according to the invention may be represented by the reaction scheme (A) which follows.

Reaction scheme A

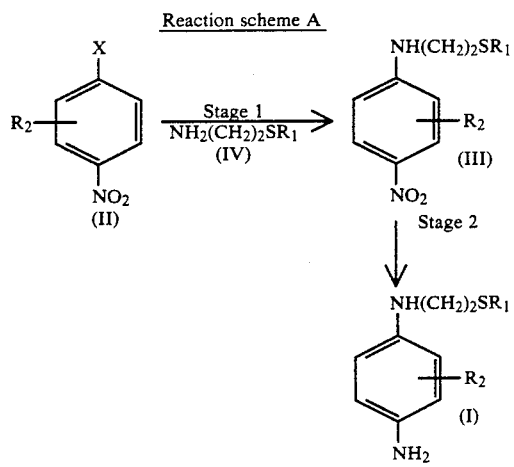

STAGE 1

The p-nitroaniline of formula (III) is prepared by the action of the amine $NH_2(CH_2)_2SR_1$ on the p-halonitrobenzene (II), in which $R_1$ and $R_2$ have the meanings defined above in the formula (I). Substitution of the halo group X is performed in water in the presence or absence of a solvent such as dimethylformamide, N-methylpyrrolidone or dioxane, the temperature of the reaction being between room temperature and the refluxing temperature of the reaction medium. The "trapping agents" for the hydrohalic acid which are used are preferably chosen from triethylamine and sodium, potassium and calcium carbonates.

STAGE 2

The reduction of the $NO_2$ group of the compound of formula (III), enabling the compound of formula (I) according to the invention to be obtained, consists in performing a reduction with hydrogen in the presence of a catalyst (Catalytic Hydrogenation, Augustine R-L, Marcel DEKKER, Inc. New York, 1965) or a reduction with iron in acetic acid or zinc in the presence of alcohol and ammonium chloride.

An especially preferred method for the preparation process according to the invention consists in preparing the amine of formula (IV) at the time of use, without isolating it, by reacting an aqueous solution of 2-aminoethanethiol hydrochloride with an aqueous sodium hydroxide solution to neutralize the hydrochloride and a halide of formula Y-R in which R has the meaning defined above and Y denotes a halogen atom preferably chosen from iodine, bromine and chlorine, the reaction temperature being below 50° C.

This preparation method may be summarized according to Reaction Scheme B.

Reaction Scheme B

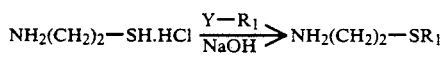

The compounds of formula (III) are new. They can be used for the direct dyeing of hair, to which they impart a yellow coloration.

The compounds of formula (I) are used, more especially, for the dyeing of keratinous fibers, and especially human keratinous fibers such as the hair.

The dyeing compositions for keratinous fibers, and especially for human hair, contain, in a medium suitable for dyeing, at least one compound of formula (I) or a corresponding salt with an acid, in amounts which are effective for dyeing.

The compounds of formula (I) are preferably used in the compositions of the invention at a concentration of between 0.02 and 6%, and preferably between 0.15 and 5%, by weight relative to the total weight of the composition The pH of the dyeing composition according to the invention is between 8 and 11, and preferably between 9 and 11.

Among alkalinizing agents which can be used, ammonia, alkali metal carbonates and alkanolamines such as mono-, di- or triethanolamine may be mentioned.

The dyeing compositions according to the invention can contain one or more compounds of formula (I). They can also contain other para-phenylenediamines, other than those defined in the formula (I), such as, for example: para-phenylenediamine, para-tolylenediamine, 2,6-dimethyl-para-phenylenediamine, 2,6-dimethyl-3-methoxy-para-phenylenediamine, 4-N,N-bis(β-hydroxyethyl)amino]aniline and 4-[N-ethyl-N-(carbamylmethyl)amino]aniline, as well as their salts.

The dyeing compositions according to the invention can also contain p-aminophenols, such as, for example: p-aminophenol, 2-methyl-4-aminophenol, 3-methyl4-aminophenol, 2-chloro-4-aminophenol, 3-chloro-4-aminophenol, 2,6-dimethyl-4-aminophenol, 3,5-dimethyl-4aminophenol, 2,3-dimethyl-4-aminophenol, 2,5-dimethyl-4aminophenol,2-hydroxymethyl-4-aminopheno1,2-(β-hydroxy-ethyl)-4-aminopheno1,2-methoxy-4-aminopheno1,3-methoxy-4-aminophenol and 2-amino-5-hydroxyphenoxyethanol, as well as their salts.

The dyeing compositions according to the invention can also contain ortho-phenylenediamines and orthoaminophenols, optionally containing substitutions on the ring or on amine groups. 1-Amino-2-hydroxybenzene, 6-methyl-1-hydroxy-2-aminobenzene and 4-methyl-1-amino-2-hydroxybenzene may be mentioned, for example.

The dyeing compositions which are the subject of the present invention generally contain, in combination with the "para" precursors consisting of the compounds of formula (I) and optionally with other para-phenylenediamines or with para-aminophenols, couplers which give dyes by oxidative coupling with the "para" precursors.

The dyes are, in particular, indoanilines, indamines or indophenols, possessing various hues, which contribute to modifying and enriching with glints the "background" colorations imparted to the hair by the condensation products of the "para" precursors with themselves.

The couplers used generally in combination with the compounds of formula (I) in the dyeing compositions according to the invention are preferably chosen from meta-diphenols, meta-aminophenols, meta-phenylenediamines, meta-acylaminophenols, meta-ureidophenols, metacarbalkoxyaminophenols, α-naphthol, heterocyclic couplers and couplers possessing an active methylene group such as β-keto compounds and pyrazolones.

Among meta-diphenols, there may be mentioned: resorcinol, 2-methylresorcinol, 5-methylresorcinol, 2,4-dihydroxyphenoxyethanol, resorcinol monomethyl ether and 2,4-dihydroxyanisole. meta-Diphenols combined with the compounds of formula (I) lead to beige-grey hues by oxidative coupling.

Among meta-aminophenols, there may be mentioned: meta-aminophenol, 2-methyl-5-aminophenol, 2-methyl-5-[N-(β-hydroxyethyl)amino]phenol, 2-methyl-5-[N-(β-methylaminoethyl)amino]phenol, 2,6-dimethyl-3-aminophenol and their salts. These couplers used with the compounds of formula (I) lead by oxidative coupling to purple hues.

Among meta-phenylenediamines, there may be mentioned:m-phenylenediamine,2,4-diaminophenoxyethanol, 2,4-dimathoxy-1,3-diaminobenzene, 1,3,5-trimethoxy-2,4-diaminobenzene, 2,4-diaminoanisole, 2-[N-(β-hydroxyethyl)amino]-4-aminophenoxyethanol, 4-[N-(β-hydroxyethyl)amino]-2-aminophenoxyethanol, 2-amino-4-[N-(β-hydroxyethy-1)amino]anisole, 4,6-bis(β-hydroxyethoxy)-1,3-diaminobenzene, 1-(β-hydroxyethoxy)-2,4-diaminobenzene and their salts. These couplers used with the compounds of formula (I) lead by oxidative coupling to blue colours.

3,4-Methylenedioxypheno-1, 3,4-methylenedioxyaniline, 2-bromo-4,5-methylenedioxyphenol, 2-chloro-4,5-methylenedioxyphenol, 6-aminobenzomorpholine and 6-hydroxybenzomorpholine may also be mentioned as couplers which are usable in the compositions of the invention.

As especially advantageous couplers, there may finally be mentioned the heterocyclic compounds corresponding to the formula:

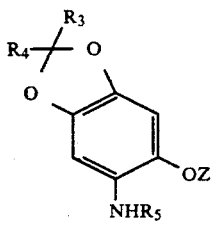

in which $R_5$ denotes a hydrogen atom, a $C_1$-$C_4$ alkyl radical, a $C_2$-$C_4$ hydroxyalkyl radical, a $C_3$ to $C_6$ polyhydroxyalkyl radical or a $C_2$-$C_6$ alkoxyalkyl radical, Z, independently of $R_5$, denotes a $C_1$ to $C_4$ alkyl radical, a $C_2$ to $C_4$ hydroxyalkyl radical, a $C_3$ to $C_6$ polyhydroxyalkyl radical, a $C_2$-$C_6$ alkoxyalkyl radical or a trifluoroethyl radical, and $R_3$ and $R_4$ denote, independently of one another, a hydrogen atom or a $C_1$ to $C_4$ alkyl radical, or one of the addition salts with an inorganic acid, and especially 4-amino-5-methoxy-1,2-methylenedioxybenzene, 4-($\beta$-hydroxyethyl)amino-5-methoxy-1,2-methylenedioxybenzene, 4-amino-5-(2',2',2'-trifluoroethoxy)-1,2-methylenedioxybenzene, 4-methylamino-5-methoxy-1,2-methylenedioxybenzene, 4-amino-5-($\beta$-hydroxyethoxy)-1,2-methylenedioxybenzene or alternatively 6-amino-5-methoxy-2-methyl-2-propyl-1,3-benzodioxole.

These couplers used with the compounds of formula (I) as well as 6-hydroxybenzomorpholine lead by oxidative coupling to green hues which are in particular demand for the production of dull hues for reducing excessively red hues, and for providing, where appropriate, a correction to the tendency shown by some dyes to redden with the passage of time.

The compositions according to the invention can also contain direct dyes preferably chosen from azo and anthraquinone dyes or nitro derivatives of the benzene series.

The addition of these direct dyes to the dyeing compositions according to the invention enables the colorations provided by the oxidation dye precursors to be varied in hue or enriched with glints.

The total amount of oxidation dyes ("para" and "ortho" compounds and couplers) used in the dyeing compositions according to the invention preferably represents from 0.1 to 7% of the total weight of the said composition.

The couplers are present in sufficient proportions to form a dye by oxidative coupling with the paraphenylenediamine of formula (I), and preferably in proportions of 0.1 to 5% by weight.

The dyeing compositions according to the invention can also contain anionic, cationic, nonionic or amphoteric surfactants or mixtures thereof. Among these surfactants, there may mentioned, more especially, alkylbenzenesulphonates, alkylnaphthalenesulphonates, fatty alcohol sulphates, ether sulphates and sulphonates, soaps, quaternary ammonium salts, fatty acid ethanolamides which are optionally oxyethylenated, polyoxyethylenated acids, alcohols and amines, polyglycerolated alcohols and polyoxyethylenated or polyglycerolated alkylphenols, as well as polyoxyethylenated alkyl sulphates.

The surfactants are present in the compositions according to the invention in proportions of between 0.5 and 40% by weight, and preferably between 2 and 30% by weight, relative to the total weight of the composition.

The dyeing compositions according to the invention can also contain organic solvents for solubilizing compounds which might be insufficiently soluble in water. Among these solvents, there may be mentioned, by way of example, $C_1$-$C_4$ lower alkanols such as ethanol and isopropanol; glycerol; aromatic alcohols such as benzyl alcohol or phenylethyl alcohol; glycols or glycol ethers such as 2-butoxyethanol, ethylene glycol, propylene glycol, diethylene glycol monoethyl ether and monomethyl ether; as well as similar products and mixtures thereof. The solvents ar preferably present in a proportion of between 1 and 40% by weight, and especially between 2 and 30% by weight, relative to the total weight of the composition.

The dyeing compositions according to the invention can contain thickening agents preferably chosen from the group composed of sodium alginate, gum arabic, cellulose derivatives such as methylcellulose, hydroxyethylcellulose, hydroxypropylcellulose, hydroxymethylcellulose and carboxymethylcellulose, acrylic acid polymers and xanthan gum. It is also possible to use inorganic thickening agents such as bentonite. These thickening agents are preferably present in proportions of between 0.1 and 5%, and especially between 0.5 and 3%, by weight relative to the total weight of the composition.

The dyeing compositions according to the invention can contain antioxidant agents chosen, in particular, from sodium sulphite, thioglycolic acid, sodium bisulphite, ascorbic acid and hydroquinone. These antioxidant agents are present in the composition in proportions of between 0.05 and 1.5% by weight relative to the total weight of the composition.

The compositions according to the invention can contain other adjuvants generally used in cosmetics, such as penetrating agents, sequestering agents, buffers and perfumes.

The dyeing compositions according to the invention may be presented in various forms, such as in the form of liquids, creams or gels, or in any other form suitable for carrying out a dyeing of keratinous fibers and, in particular, of human hair. They can also be packaged in aerosol cans in the presence of a propellant agent.

The subject of the present invention is also a process for dyeing keratinous fibers, and especially human hair, characterized in that a dyeing composition containing a para type oxidation dye precursor of formula (I) is mixed at the time of use with an oxidizing solution in a sufficient amount to form the dye, in that the mixture obtained is applied on the hair, in that it is left in place for 10 to 40 minutes, and preferably for 15 to 30 minutes, in that the hair is rinsed, in that it is washed with shampoo, in that it is rinsed again and, finally, in that it is dried.

The oxidizing solution contains oxidizing agents such as hydrogen peroxide, urea peroxide or persalts such as ammonium persulphate. A "20 volumes" hydrogen peroxide solution is preferably used.

Another special form of hair dyeing process according to the invention consists in applying on the hair the para type oxidation dye precursor of formula (I) by means of a composition defined above and, in a second stage, the coupler or couplers is/are applied on the hair, the oxidizing agent being present in the composition applied in the second stage or alternatively applied on the hair itself in a third stage, and the conditions of exposure, drying and washing being identical to those stated in the above process.

The examples which follow serve to give a better illustration of the invention, but in no way limit the scope of the latter.

PREPARATION EXAMPLE 1

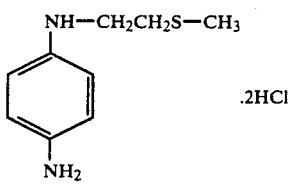

.2HCl

Preparation of 4-[β-(methylthio)ethylamino]aniline dihydrochloride

FIRST STAGE

Preparation of 4-nitro-N-β-(methylthio)ethyl]aniline

A solution of 0.4 mole of sodium hydroxide in 100 ml of water is added dropwise at 30° C. to a solution of 0.4 mole (45.4 g ) of 2-aminoethanethiol hydrochloride and 0.4 mole (56.8 g) of methyl iodide in 100 ml of water. After a further hour of stirring at 40° C., 0.15 mole (21.2 g) of 4-fluoronitrobenzene and 42 ml of triethylamine are added.

The reaction mixture is heated for 3 hours on a boiling waterbath and then left overnight at room temperature; after acidification, it is extracted with ethyl acetate.

After the organic phase is dried, an oil is obtained by evaporating off the ethyl acetate under vacuum. The unreacted 4-fluoronitrobenzene may be recovered by extraction with ethyl ether of the solution prepared by dissolving the oil obtained in 100 ml of concentrated hydrochloric acid. By neutralization of the aqueous phase, followed by extraction with ethyl ether, the expected product is obtained, and this is purified by chromatography on a silica column (eluent cyclohexane/ethyl acetate 75:25).

Analysis of the product thus purified gives the following results:

| Analysis | Calculated for C9H12N2O2S | Found |
| --- | --- | --- |
| C % | 50.94 | 51.10 |
| H % | 5.70 | 5.74 |
| N % | 13.20 | 13.25 |
| O % | 15.08 | 15.20 |
| S % | 15.08 | 15.15 |

SECOND STAGE

Preparation of 4-[β-(methylthio)ethylamino]aniline 0.8 g of ammonium chloride and 20 g of powdered zinc are added to 44 ml of aqueous-alcoholic solution (10% of water, 90% of alcohol). This mixture is brought to reflux with stirring, and 0.04 mole (8.5 g) of 4-nitro-N-[[β-(methylthio)ethyl]aniline is added, the addition being regulated so as to maintain the reflux without heating. The decolorized reaction medium is filtered while boiling into a flask containing 8.5 ml of strength hydrochloric acid. The expected product precipitates in the form of a dihydrochloride. It is dried under vacuum at 55° C.

Analysis of the product obtained gives the following results:

| Analysis | Calculated for C9H16Cl2N2S | Found |
| --- | --- | --- |
| C % | 42.35 | 42.27 |
| H % | 6.32 | 6.39 |
| N % | 10.98 | 11.12 |
| S % | 12.56 | 12.44 |
| Cl % | 27.78 | 28.08 |

PREPARATION EXAMPLE 2

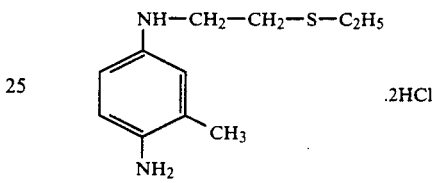

.2HCl

Preparation of 2-methyl-4-[β-(ethylthio)ethylamino]aniline dihydrochloride

FIRST STAGE

Preparation of 3-methyl-4-nitro-N-[β-(ethylthio)ethyl]aniline 0.26 mole (40.6 g) of ethyl iodide is added to a solution of 0.27 mole of sodium hydroxide pellets and 0.25 mole (28.4 g) of 2-aminoethanethiol hydrochloride in 100 ml of water while the temperature is maintained at 30° C. After a further 2 hours of stirring at 40° C., 25 ml of dioxane are added, followed by 0.12 mole (18.6 g) of 5-fluoro-2-nitrotoluene and 56 ml of triethylamine.

The reaction mixture is heated for 5 hours under reflux. After dilution with 250 g of an ice/water mixture, the reaction medium is neutralized. The oily phase obtained after settling has taken place is dissolved in 100 ml of 36% strength hydrochloric acid. The hydrochloride of the expected product precipitates.

By dissolution in 150 ml of hot water followed by addition of 10 ml of a 20% strength ammonia solution, the expected product precipitates; it melts below 50° C.

Analysis of the product obtained gives the following results:

| Analysis | Calculated for C11H16N2O2S | Found |
| --- | --- | --- |
| C % | 54.97 | 54.80 |
| H % | 6.72 | 6.74 |
| N % | 11.66 | 11.61 |
| O % | 13.32 | 13.25 |
| S % | 13.34 | 13.54 |

SECOND STAGE

Preparation of 2-methyl-4-[β-(ethylthio)ethylamino]aniline dihydrochloride

A reaction mixture composed of 0.041 mole (10 g) of 3-methyl-4-nitro-N-[β-(ethylthio)ethyl]aniline and 4.5 g of palladium on charcoal (10% palladium) in 100 ml of absolute ethanol is subjected to a pressure of 50 kg of hydrogen in an autoclave. The reaction mixture is left for 2 hours without heating. The reaction medium is filtered into a flask containing 16 ml of a solution of hydrochloric acid in absolute ethanol. The hydrochloride of the expected product precipitates and is dried under vacuum at 40° C. It is recrystallized in 125 ml of 96° strength ethanol.

Analysis of the product obtained gives the following results:

| Analysis | Calculated for $C_{11}H_{20}Cl_2N_2S$ | Found |
|---|---|---|
| C % | 46.64 | 46.57 |
| H % | 7.12 | 7.15 |
| N % | 9.89 | 9.83 |
| S % | 11.32 | 11.24 |
| Cl % | 25.03 | 25.23 |

PREPARATION EXAMPLE 3

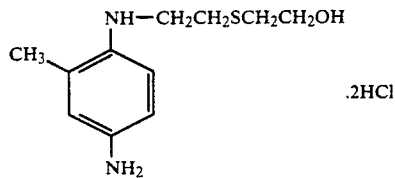

.2HCl

Preparation of 3-methyl-4-[β-(β'-hydroxyethylthio)ethylamino]aniline dihydrochloride

FIRST STAGE

Preparation of 2-methyl-4-nitro-N-[β-(β'-hydroxyethylthio)ethyl]aniline 0.21 mole (26.3 g) of glycol bromohydrin is added dropwise at 40° C. to a solution of 0.22 mole of sodium hydroxide pellets and 0.2 mole (22.7 g) of 2-aminoethanethiol hydrochloride in 100 ml of water. Heating is maintained at 40° C. for 30 minutes after completion of the addition. 0.12 mole (18.6 g) of 4-fluoro-3-methylnitrobenzene, 56 ml of triethylamine and 50 ml of dioxane are added. The reaction medium is heated for 12 hours under reflux. After evaporation to dryness under vacuum, the residue is diluted with 100 ml of water to which 20 ml of 36% strength hydrochloric acid has been added. The expected product precipitates. When recrystallized in 96° strength alcohol, it melts at 90° C.

Analysis of the product obtained gives the following results:

| Analysis | Calculated for $C_{11}H_{16}N_2O_3S$ | Found |
|---|---|---|
| C % | 51.54 | 51.31 |
| H % | 6.29 | 6.35 |
| N % | 10.93 | 10.81 |
| O % | 18.72 | 18.49 |
| S % | 12.51 | 12.38 |

SECOND STAGE

Preparation of 3-methyl-4-[β-(β'-hydroxyethylthio)ethylamino]aniline dihydrochloride A reaction mixture consisting of 0.0125 mole (3.3 g) of 2-methyl-4-nitro-N-[β-(β'-hydroxyethylthio)ethyl]aniline and 1.5 g of palladium on charcoal (10% palladium) in 70 ml of absolute ethanol is subjected to a pressure of 50 kg of hydrogen for 3 hours without heating. The reaction medium is filtered into a flask containing 5 ml of a solution of hydrochloric acid in absolute ethanol. The hydrochloride of the expected product precipitates.

Analysis of the product obtained after drying under vacuum gives the following results:

| Analysis | Calculated for $C_{11}H_{20}Cl_2N_2OS$ | Found |
|---|---|---|
| C % | 44.14 | 43.91 |
| H % | 6.74 | 6.77 |
| N % | 9.36 | 9.28 |
| O % | 5.35 | 5.65 |
| S % | 10.71 | 10.58 |
| Cl % | 23.69 | 23.52 |

PREPARATION EXAMPLE 4

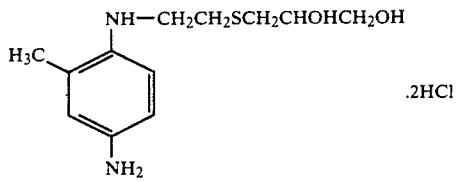

.2HCl

Preparation of 3-methyl-4-[β-(β', γ'-dihydroxypropylthio)ethylamino]aniline dihydrochloride hemihydrate

FIRST STAGE

Preparation of 2-methyl-4-nitro-N-[β-(β', γ',-dihydroxypropylthio)ethyl]aniline 0.42 mole (46.4 g) of 3-chloro-1,2-propanediol is added dropwise to a solution of 0.44 mole of sodium hydroxide pellets and 0.40 mole (45.4 g) of 2-aminoethanethiol hydrochloride in 200 ml of water while the temperature is maintained at 50°.

Stirring at 50° is maintained for 2 hours after completion of the introduction. 50 ml of dioxane, 0.2 mole (31.0 g) of 4-fluoro-3-methylnitrobenzene and 111 ml of triethylamine are added.

The reaction mixture is heated for about 10 hours under reflux. After evaporation to dryness under reduced pressure, the oily residue is diluted with 100 ml of water, acidified with 10 ml of 36% strength hydrochloric acid and extracted with ethyl acetate.

After the organic phase is dried and the ethyl acetate evaporated off under vacuum, the expected product is obtained, and this is purified by chromatography on a silica gel column (eluent: cyclohexane/ethyl acetate 50:50). When recrystallized from ethyl acetate, it melts at 100° C.

Analysis of the product obtained gives the following results:

| Analysis | Calculated for $C_{12}H_{18}N_2O_4S$ | Found |
|---|---|---|
| C % | 50.33 | 50.35 |
| H % | 6.34 | 6.33 |
| N % | 9.78 | 9.64 |
| O % | 22.35 | 22.34 |
| S % | 11.20 | 11.24 |

SECOND STAGE

Preparation of 3-methyl-4-[β-(β',γ'-dihydroxypropylthio) ethylamino]aniline dihydrochloride hemihydrate A mixture of 5 ml of 96° strength alcohol, 0.5 ml of water, 0.1 g of ammonium chloride and 2.5 g of finely powdered zinc is heated to reflux of the alcohol.

0.005 mole (1.4 g) of 2-methyl-4-nitro-N-[β(β-(β', γ'-dihydroxypropylthio)ethyl]aniline is added portionwise so as to maintain the reflux without heating. The decolorized reaction medium is heated under reflux for a further 10 min after completion of the addition, and is then filtered while boiling into a flask containing 1.3 ml of 36% strength hydrochloric acid.

After evaporation to dryness under vacuum, the expected product is obtained in the form of the dihydrochloride hemihydrate.

Analysis of the product obtained gives the following results:

| Analysis | Calculated for $C_{12}H_{22}N_2O_2SCl_2 \cdot \frac{1}{2}H_2O$ | Found |
|---|---|---|
| C % | 42.60 | 42.30 |
| H % | 6.85 | 6.80 |
| N % | 8.28 | 8.13 |
| O % | 11.82 | 11.74 |
| S % | 9.48 | 9.45 |
| Cl % | 20.96 | 21.00 |

APPLICATION EXAMPLE 1

The following dyeing mixture is prepared:

| | |
|---|---|
| 4-[β-(Methylthio)ethylamino]aniline dihydrochloride | 1.0 g |
| Nonylphenol oxyethylenated with 4 moles of ethylene oxide, sold by the company RHONE POULENC under the name CEMULSOL NP 4 | 12.0 g |
| Nonylphenol oxyethylenated with 9 moles of ethylene oxide, sold by the company RHONE POULENC under the name CEMULSOL NP 9 | 15.0 g |
| Oleyl alcohol polyglycerolated with 2 moles of glycerol | 1.5 g |
| Oleyl alcohol polyglycerolated with 4 moles of glycerol | 1.5 g |
| Propylene glycol | 6.0 g |
| Ethylenediaminetetraacetic acid, sold under the name TRILON B | 0.12 g |
| Ammonia solution, 22° Bé strength | 11.0 g |
| Water q.s. | 100.0 g |
| pH 9.5 | |

100 g of "20 volumes" hydrogen peroxide are added at the time of use.

When applied for 20 minutes at 35° C. on hair which is naturally 90% white, the mixture imparts thereto, after shampooing and rinsing, a dark bluish-grey coloration.

APPLICATION EXAMPLE 2

The following dyeing mixture is prepared:

| | |
|---|---|
| 3-Methyl-4-[β-(β'-hydroxyethylthio)-ethylamino]aniline | 2.0 g |
| Cetyl/stearyl alcohol, sold by the company CONDEA under the name ALFOL C 16/18 | 19.0 g |
| 2-Octyldodecanol, sold by the company HENKEL under the name EUTANOL G | 4.5 g |
| Cetyl/stearyl alcohol containing 15 moles of ethylene oxide, sold by the company HENKEL under the name MARGITAL C.S. | 2.5 g |
| Ammonium lauryl sulphate | 10.0 g |
| Cationic polymer possessing the following repeat unit: | 4.0 g |

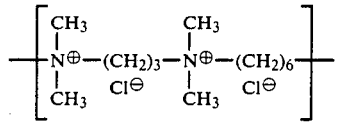

| | |
|---|---|
| Benzyl alcohol | 2.0 g |
| Ammonia solution 22°Bé strength | 11.0 ml |
| Ethylenediaminetetraacetic acid, sold under the name TRILON B | 1.0 g |
| Sodium bisulphite, 35°Bé strength | 1.2 g |
| Water q.s. | 100.0 g |
| pH 9 | |

100 g of "20 volumes" hydrogen peroxide are added at the time of use.

When applied for 20 minutes at 35° C. on bleached hair, the mixture imparts thereto, after shampooing and rinsing, a dark grey-purple coloration.

APPLICATION EXAMPLE 3

The following dyeing mixture is prepared:

| | |
|---|---|
| 4-[β-(Methylthio)ethylamino]aniline dihydrochloride | 1.27 g |
| 2-(2,4-Diaminophenoxy)ethanol dihydrochloride | 1.21 g |
| Nonylphenol oxyethylenated with 4 moles of ethylene oxide, sold by the company RHONE POULENC under the name CEMULSOL NP 4 | 12.0 g |
| Nonylphenol oxyethylenated with 9 moles of ethylene oxide, sold by the company RHONE POULENC under the name CEMULSOL NP 9 | 15.0 g |
| Oleyl alcohol polyglycerolated with 2 moles of glycerol | 1.5 g |
| Oleyl alcohol polyglycerolated with 4 moles of glycerol | 1.5 g |
| Propylene glycol | 6.0 g |
| Ethylenediaminetetraacetic acid, sold under the name TRILON B | 0.12 g |
| Ammonia solution 22° Bé strength | 11.0 g |
| Thioglycolic acid | 0.6 g |
| Water q.s. | 100.0 g |
| pH 9 | |

90 g of "20 volumes" hydrogen peroxide are added at the time of use.

When applied for 20 minutes at 35° C. on hair which is naturally 90% white, the mixture imparts thereto, after shampooing and rinsing, a deep blue coloration.

APPLICATION EXAMPLE 4

| | |
|---|---|
| 2-Methyl-4-[β-(ethylthio)ethylamino]-aniline dihydrochloride | 0.85 g |
| 1,3-Diamino-2,4-dimethoxybenzene dihydrochloride | 0.72 g |
| Acrylic acid homopolymer crosslinked with a polyfunctional agent, sold by the company GOODRICH CHEMICALS under the name CARBOPOL 934 | 3.0 g |
| Ethanol, 96° strength | 11.0 g |
| 2-Butoxyethanol | 5.0 g |
| Trimethylcetylammonium bromide | 2.0 g |
| Ethylenediaminetetraacetic acid, sold under the name TRILON B | 0.2 g |
| Ammonia solution, 22° Bé strength | 10.0 g |
| Sodium bisulphite, 35° Bé strength | 1.0 g |
| Water q.s. | 100.0 g |
| pH 9.1 | |

100 g of "20 volumes" hydrogen peroxide are added at the time of use.

When applied for 20 minutes at 35° C. on bleached hair, the mixture imparts thereto, after shampooing and rinsing, a dark blue coloration.

APPLICATION EXAMPLE 5

| | |
|---|---|
| 3-Methyl-4-[β-(β'-hydroxyethylthio)-ethylamino]aniline dihydrochloride | 2.0 g |
| 4,6-Bis(β-hydroxyethoxy)-1,3-phenylene-diamine dihydrochloride | 2.02 g |
| Nonylphenol oxyethylenated with 4 moles of ethylene oxide, sold by the company RHONE POULENC under the name CEMULSOL NP 4 | 12.0 g |
| Nonylphenol oxyethylenated with 9 moles of ethylene oxide, sold by the company RHONE POULENC under the name CEMULSOL NP 9 | 15.0 g |
| Oleyl alcohol polyglycerolated with 2 moles of glycerol | 1.5 g |
| Oleyl alcohol polyglycerolated with 4 moles of glycerol | 1.5 g |
| Propylene glycol | 6.0 g |
| Ethylenediaminetetraacetic acid, sold under the name TRILON B | 0.12 g |
| Ammonia solution 22° Bé strength | 11.0 g |
| Water q.s. | 100.0 g |
| pH 9.5 | |

100 g of "20 volumes" hydrogen peroxide are added at the time of use.

When applied for 25 minutes at 35° C. on bleached hair, the mixture imparts thereto, after shampooing and rinsing, a dark purple-blue coloration.

APPLICATION EXAMPLE 6

| | |
|---|---|
| 3-Methyl-4-[β-(β'-hydroxyethylthio)-ethylamino]aniline dihydrochloride | 0.75 g |
| 2-Methoxy-4,5-methylenedioxyaniline hydrochloride | 0.51 g |
| Oleyl alcohol polyglycerolated with 2 moles of glycerol | 4.5 g |
| Oleyl alcohol polyglycerolated with 4 moles of glycerol | 4.5 g |
| Oleylamine oxyethylenated with 12 moles of ethylene oxide, sold by the company ARMOON HESS CHEMICAL Ltd under the name ETHOMEEN O 12 | 4.5 g |
| Coconut diethanolamide, sold by the company HENKEL under the name COMPERLAN KD | 9.0 g |
| Propylene glycol | 4.0 g |
| 2-Butoxyethanol | 8.0 g |
| Ethanol, 96° strength | 6.0 g |
| Diethylenetriaminepentaacetic acid pentasodium salt, sold by the company PROTEX under the name MASQUOL DTPA | 2.0 g |
| Hydroquinone | 0.15 g |
| Sodium bisulphite solution, 35° Bé strength | 1.3 g |
| Ammonia solution, 22° Bé strength | 10.0 g |
| Water q.s. | 100.0 g |
| pH 10 | |

100 g of "20 volumes" hydrogen peroxide are added at the time of use.

When applied for 20 minutes at 35° C. on bleached hair, the mixture imparts thereto, after shampooing and rinsing, a medium yellow-green coloration.

APPLICATION EXAMPLE 7

The following dyeing mixture is prepared:

| | |
|---|---|
| 4-[β-(Methylthio)ethylamino]aniline dihydrochloride | 0.64 g |
| 6-Hydroxybenzomorpholine | 0.38 g |
| Oleyl alcohol polyglycerolated with 2 moles of glycerol | 4.5 g |
| Oleyl alcohol polyglycerolated with 4 moles of glycerol | 4.5 g |
| Oleylamine oxyethylenated with 12 moles of ethylene oxide, sold by the company ARMOON HESS CHEMICAL Ltd under the name ETHOMEEN O 12 | 4.5 g |
| Coconut diethanolamide, sold by the company HENKEL under the name COMPERLAN KD | 9.0 g |
| Propylene glycol | 4.0 g |
| 2-Butoxyethanol | 8.0 g |
| Ethanol, 96° strength | 6.0 g |
| Diethylenetriaminepentaacetic acid pentasodium salt, sold by the company PROTEX under the name MASQUOL DTPA | 2.0 g |
| Hydroquinone | 0.15 g |
| Sodium bisulphite solution, 35° Bé strength | 1.3 g |
| Ammonia solution, 22° Bé strength | 10.0 g |
| Water q.s. | 100.0 g |
| pH 10 | |

100 g of "20 volumes" hydrogen peroxide are added at the time of use.

When applied for 20 minutes at 35° C. on hair which is naturally 90% white, the mixture imparts thereto, after shampooing and rinsing, a light olive-green coloration.

APPLICATION EXAMPLE 8

The following dyeing mixture is prepared:

| | |
|---|---|
| 3-Methyl-4-[β-(β'-hydroxyethylthio)-ethylamino]aniline dihydrochloride | 1.0 g |
| 2-Methoxy-4,5-methylenedioxyaniline hydrochloride | 0.67 g |
| 2,6-Bis(β-hydroxyethylamino)nitrobenzene | 0.1 g |
| Cetyl/stearyl alcohol, sold by the company CONDEA under the name ALFOL C 16/18 | 8.0 g |
| Sodium cetyl/stearyl sulphate, sold by the company HENKEL under the name CIRE DE LANETTE E | 0.5 g |
| Ethoxylated castor oil, sold by the company RHONE POULENC under the name CEMULSOL B | 1.0 g |

| -continued | |
|---|---|
| Oleic diethanolamide | 1.5 g |
| Diethylenetriaminepentaacetic acid pentasodium salt | 2.5 g |
| Ammonia solution, 22° Bé strength | 11.0 g |
| Water q.s. | 100.0 g |
| pH 10.2 | |

100 g of "20 volumes" hydrogen peroxide are added at the time of use.

When applied for 15 minutes at 35° C. on hair which is naturally 90% white, the mixture imparts thereto, after shampooing and rinsing, a light brown coloration.

The following dyeing mixture is prepared:

| 2-Methyl-4-[β-(ethylthio)ethylamino]-aniline dihydrochloride | 0.26 g |
|---|---|
| Sesamol | 0.155 g |
| meta-Aminophenol | 0.185 g |
| 4-Amino-2-hydroxytoluene | 0.15 g |
| Cetyl/stearyl alcohol | 19.0 g |
| 2-Octyldodecanol | 4.5 g |
| Cetyl/stearyl alcohol containing 15 moles of ethylene oxide | 2.5 g |
| Ammonium lauryl sulphate | 10.0 g |
| Cationic polymer possessing the following repeated unit: | 4.0 g |
| 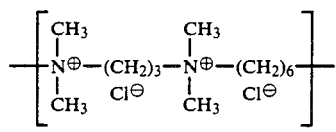 | |
| Benzyl alcohol | 2.0 g |
| Ammonia solution, 22°Bé strength | 11 ml |
| Ethylenediaminetetraacetic acid | 1.0 g |
| Sodium bisulphite, 35°Bé strength | 1.2 g |
| Water q.s. | 100.0 g |
| pH 9.3 | |

70 g of "20 volumes" hydrogen peroxide are added at the time of use.

When applied for 25 minutes at 35° C. on bleached hair, the mixture imparts thereto, after shampooing and rinsing, a grey red-brown coloration.

APPLICATION EXAMPLE 10

The following dyeing mixture is prepared:

| 4-[β-(Methylthio)ethylamino]aniline dihydrochloride | 0.44 g |
|---|---|
| p-Aminophenol | 0.16 g |
| Resorcinol | 0.22 g |
| 4-(β-Hydroxyethylamino)-2-hydroxytoluene | 0.27 g |
| Nonylphenol oxyethylenated with 4 moles of ethylene oxide | 12.0 g |
| Nonylphenol oxyethylenated with 9 moles of ethylene oxide | 15.0 g |
| Oleyl alcohol polyglycerolated with 2 moles of glycerol | 1.5 g |
| Oleyl alcohol polyglycerolated with 4 moles of glycerol | 1.5 g |
| Propylene glycol | 6.0 g |
| Ethylenediaminetetraacetic acid | 0.12 g |
| Ammonia solution, 22° Bé strength | 11.0 g |
| Thioglycolic acid | 0.6 g |
| Water q.s. | 100.0 g |
| pH 10.1 | |

100 g of "20 volumes" hydrogen peroxide are added at the time of use.

When applied for 20 minutes at 35° C. on bleached hair, the mixture imparts thereto, after shampooing and rinsing, a deep orange-red coloration.

APPLICATION EXAMPLE 11

The following dyeing mixture is prepared:

| 4-Nitro-N-[β-(methylthio)ethyl]aniline (intermediate compound of Example 1) | 0.3 g |
|---|---|
| Ethanol, 96° strength | 15.0 g |
| Hydroxyethylcellulose, sold by the company UNION CARBIDE under the name CELLOSIZE W.P. P3 | 2.0 g |
| Ammonium lauryl sulphate | 5.0 g |
| Ammonia solution, 22° Bé strength | 0.5 g |
| Water q.s. | 100.0 g |
| pH 9 | |

When applied for 20 minutes at 37° C. on hair which is naturally 90% white, this mixture imparts thereto, after shampooing and rinsing, a canary-yellow coloration.

APPLICATION EXAMPLE 12

The following dyeing mixture is prepare:

| 3-Methyl-4-[β-(β',γ'-dihydroxypropylthio)-ethylamino]aniline dihydrochloride hemihydrate | 0.84 g |
|---|---|
| 4-(β-Hydroxyethylamino)-2-hydroxytoluene | 0.42 g |
| Oleyl alcohol polyglycerolated with 2 moles of glycerol | 4.5 g |
| Oleyl alcohol polyglycerolated with 4 moles of glycerol | 4.5 g |
| Oleylamine oxyethylenated with 12 moles of ethylene oxide, sold by the company ARMOON HESS CHEMICAL Ltd under the name ETHOMEEN O 12 | 4.5 g |
| Coconut diethanolamide, sold by the company HENKEL under the name COMPERLAN KD | 9.0 g |
| Propylene glycol | 4.0 g |
| 2-Butoxyethanol | 8.0 g |
| Ethanol, 96° strength | 6.0 g |
| Diethylenetriaminepentaacetic acid pentasodium salt, sold by the company PROTEX under the name MASQUOL DTPA | 2.0 g |
| Hydroquinone | 0.15 g |
| Sodium bisulphite solution, 35° Bé strength | 1.3 g |
| Ammonia solution, 22° Bé strength | 10.0 g |
| Water q.s. | 100.0 g |
| pH 10 | |

100 g of "20 volumes" hydrogen peroxide are added at the time of use. When applied for 20 minutes at 35° C. on bleached hair, the mixture imparts thereto, after shampooing and rinsing, a deep purple coloration.

We claim:

1. Compound which corresponds to the formula:

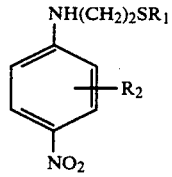

in which $R_1$ denotes an alkyl, hydroxyalkyl or polyhydroxyalkyl radical and $R_2$ denotes a hydrogen atom or an alkyl radical, as well as the corresponding salts with acids.

2. Dyeing composition for direct dyeing of human hair, which contains, in a medium suitable for dyeing, an effective amount at least one compound in accordance with claim 1.